US010004465B2

(12) United States Patent
Krauss et al.

(10) Patent No.: US 10,004,465 B2
(45) Date of Patent: Jun. 26, 2018

(54) METHOD FOR DETERMINING AN X-RAY TUBE CURRENT PROFILE, COMPUTER PROGRAM, DATA CARRIER AND X-RAY IMAGE RECORDING DEVICE

(71) Applicant: Siemens Aktiengesellschaft, München (DE)

(72) Inventors: Andreas Krauss, Fuerth (DE); Rainer Raupach, Heroldsbach (DE); Bernhard Schmidt, Fuerth (DE)

(73) Assignee: Siemens Aktiengesellschaft, Munich (DE)

( * ) Notice: Subject to any disclaimer, the term of this patent is extended or adjusted under 35 U.S.C. 154(b) by 171 days.

(21) Appl. No.: 15/058,210

(22) Filed: Mar. 2, 2016

(65) Prior Publication Data

US 2016/0262714 A1    Sep. 15, 2016

(30) Foreign Application Priority Data

Mar. 12, 2015   (DE) ........................ 10 2015 204 449

(51) Int. Cl.
*A61B 6/00*    (2006.01)
*A61B 6/03*    (2006.01)
*A61B 5/00*    (2006.01)

(52) U.S. Cl.
CPC ............ *A61B 6/032* (2013.01); *A61B 5/0035* (2013.01); *A61B 5/0064* (2013.01); *A61B 6/544* (2013.01); *A61B 6/545* (2013.01)

(58) Field of Classification Search
CPC ..... A61B 6/5217; A61B 6/467; A61B 6/5205; A61B 6/032; A61B 6/544; A61B 6/545; A61B 5/0064; A61B 5/0035
See application file for complete search history.

(56) References Cited

U.S. PATENT DOCUMENTS 6,385,280 B1 * 5/2002 Bittl ........................ A61B 6/032
378/106
6,490,337 B1   12/2002 Nagaoka et al.
(Continued)

FOREIGN PATENT DOCUMENTS

DE   102004042790 A1   3/2006
JP        4519254 B2    8/2010
(Continued)

OTHER PUBLICATIONS

German Office Action dated Oct. 30, 2015.
Chinese Office Action and English translation thereof dated Feb. 13, 2017.

*Primary Examiner* — Courtney Thomas
(74) *Attorney, Agent, or Firm* — Harness, Dickey & Pierce, P.L.C.

(57) ABSTRACT

A method for determining a tube current profile for the recording of at least one X-ray image of body region of a patient with an X-ray image recording device, a corresponding computer program, a machine-readable data carrier and an X-ray image recording device are disclosed. The method includes acquisition of an image recorded via an optical sensor wherein the image has a field of view including at least the body region of the patient to be depicted by way of an X-ray image; determination of at least one piece of patient-specific, body-related information for the patient from the image; determination of an X-ray attenuation distribution of the patient at least for the body region to be depicted by way of an X-ray image with reference to the at least one piece of patient-specific, body-related information; and determination of the tube current profile with reference to the X-ray attenuation distribution determined.

26 Claims, 3 Drawing Sheets

(56) References Cited

U.S. PATENT DOCUMENTS

2008/0101538 A1    5/2008  Schliermann
2011/0194670 A1    8/2011  Borghese
2014/0355735 A1*  12/2014  Choi ..................... A61B 6/544
                                                         378/8

FOREIGN PATENT DOCUMENTS

JP    2012024404 A    2/2012
KR    20140141186 A   12/2014

* cited by examiner

METHOD FOR DETERMINING AN X-RAY TUBE CURRENT PROFILE, COMPUTER PROGRAM, DATA CARRIER AND X-RAY IMAGE RECORDING DEVICE

PRIORITY STATEMENT

The present application hereby claims priority under 35 U.S.C. § 119 to German patent application number DE 102015204449.1 filed Mar. 12, 2015, the entire contents of which are hereby incorporated herein by reference.

FIELD

At least one embodiment of the invention generally relates to a method for determining a tube current profile, a corresponding computer program, a data carrier and/or an X-ray image recording device.

BACKGROUND

Imaging X-ray devices, such as, for example, a C-arm X-ray apparatus or a computed tomography apparatus are increasingly being used for the clarification of medical questions. The use of X-rays exposes patients to increasing amounts of radiation so that an appropriate and dose-optimized usage as defined by the ("as low as reasonably achievable") is necessary in each examination. Accordingly, the aim of medical imaging is to apply the lowest possible X-ray dose to a patient for the generation of one or more X-ray images.

Different measures are used to achieve this. One method for dose optimization is to adapt the X-ray tube current to individual X-ray attenuation properties of a patient.

To this end, modern X-ray image recording devices have automatic dose control systems which are used to adapt the X-ray tube current for an X-ray scan or an X-ray image recording automatically or semi-automatically to the X-ray attenuation properties of the patient. For the determination of a suitable tube current profile, it is advisable to find a middle way between the lowest possible radiation exposure and sufficient image quality to enable the medical question to be resolved. Consequently, an automatic dose control system results in a tube current profile for an X-ray image recording, which determines, in dependence on the X-ray attenuation distribution of a patient for each position along the patient's body axis and/or each direction of projection, the values for the tube current that produce the desired image quality. The term tube current modulation is also used in this context.

Known automatic dose control systems are based on topograms. A topogram corresponds to a conventional, two-dimensional X-ray superposition recording. It measures the individual X-ray attenuation distribution due to a patient in a specific direction of projection in which the X-rays pass through the patient and depicts this by way of different grey values. An automatic dose control system uses this X-ray attenuation to determine a suitable tube current profile or for tube current modulation. In a known method, before recording an X-ray image, one topogram is recorded of a patient in the lateral direction and one in the anterior-posterior direction and in each case the X-ray attenuation distribution is determined with reference to the grey-value distribution in the corresponding direction for the patient.

The decisive quality feature of an X-ray image recorded with the X-ray image recording device is the image noise. The image noise is defined as a desired value corresponding to the medical question and the automatic dose control system uses the reference values for tube current and X-ray attenuation corresponding to the desired image quality, which may be prespecified by a user or made available to him for selection, and the X-ray attenuation distribution derived from the topograms to determine an optimal tube current profile for the patient. In other words, the automatic dose control system uses the X-ray attenuation distribution of a patient for each position along the patient's body axis and/or each direction of projection to determine the values for the tube current which provide the desired image quality. Corresponding modulation of the tube current during the X-ray scans ensures that the desired image quality of the X-ray images is achieved with a reduced X-ray dose.

SUMMARY

The inventors have recognized that one disadvantage of this known procedure for dose optimization is that, in addition to the actual X-ray image recording with the X-ray image recording device, the recording of topograms results in an additional, not insignificant, proportion of the overall dose for the patient.

At least one embodiment of the present invention involves achieving an adaptation of the X-ray tube current profile to the individual X-ray attenuation properties of a patient, with which the total dose applied to the patient can be further reduced.

At least one embodiment of the invention is directed to a method; at least one embodiment of the invention is directed to a computer program; at least one embodiment of the invention is directed to a machine-readable data carrier and at least one embodiment of the invention is directed to an X-ray image recording device.

The following describes embodiments according to a method and a device. Features, advantages or alternative embodiments mentioned here can also be transferred to the other subject-matter claimed and vice versa. In other words, the substantive claims (which relate, for example, to a device) can also be developed with the features described or claimed in connection with the system or network. The corresponding functional features of the method are formed by corresponding substantive modules.

At least one embodiment of the invention is based on the acquisition of an image, which was recorded via an optical sensor. This image comprises at least the body region of a patient, which is to be depicted in an X-ray image, which is to be recorded with an X-ray image recording device. Furthermore, at least one piece of patient-specific, body-related information is derived from the image. The inventors have now recognized that the patient-specific, body-related information on the patient can be used to determine an X-ray attenuation distribution for the patient at least for the body region of the patient to be depicted by way of an X-ray image and use this to determine an X-ray tube current profile.

According to a first aspect of at least one embodiment, the optical sensor records a three-dimensional image of the patient of at least the body region of the patient to be depicted. Accordingly, the optical sensor in this embodiment of the invention is designed for contactless sampling of the surface of an object. The three-dimensional image contains depth information on the image content depicted. In other words, the three-dimensional image also contains information on the distance of the patient from the sensor for each pixel or for each image point. Unlike the case with a two-dimensional image, which only depicts an object in two dimensions with grey values or color values, the three-dimensional image is particularly valuable due to its increased information content with respect to the at least one piece of patient-specific, body-related information.

At least one embodiment of the invention further relates to a computer program with a program code for carrying out all method steps of the method according to the invention when the program is executed in a computer. This means the method can be carried out reproducibly and with little susceptibility to errors on different computers.

At least one embodiment of the invention further relates to a machine-readable data carrier on which the above-described computer program is stored.

At least one embodiment of the invention further relates to an X-ray image recording device with an X-ray source, an X-ray detector and a computer embodied to carry out a method according to at least one embodiment of the invention.

The X-ray image recording device is an X-ray apparatus, which is designed to record a plurality of X-ray projections from different projection angles, for example a computed tomography apparatus with an annular rotating frame or a C-arm X-ray apparatus. The recordings can be generated during a, in particular continuous, rotary movement of a recording unit with an X-ray source and an X-ray detector that interacts with the X-ray source. The X-ray source can in particular be an X-ray tube with a rotary anode. The X-ray detector for a computed tomography apparatus is, for example, a line detector with a plurality of lines. An X-ray detector for a C-arm X-ray apparatus is, for example, a flat panel detector. The X-ray detector can be embodied as both energy-resolving and counting.

At least one embodiment of the invention further relates to an X-ray image recording device with an X-ray source, an X-ray detector and a computer, wherein the computer is embodied to acquire an image of a patient recorded via an optical sensor, wherein the image has a field of view including at least one body region to be depicted via X-ray image recording, to determine at least one piece of patient-specific, body-related information for the patient from the image, to determine an X-ray attenuation distribution of the patient at least for the body region to be depicted by way of an X-ray image with reference to the at least one piece of patient-specific, body-related information and to determine a tube current profile with reference to the X-ray attenuation distribution determined for the recording of the X-ray image.

At least one embodiment of the invention further relates to an X-ray image recording device for recording at least one X-ray image of a body region of a patient, comprising:
 an X-ray source;
 an X-ray detector; and
 a processor and a memory, embodied to determine a tube current profile for recording of at least one X-ray image of a body region of a patient with an X-ray image recording device, the memory containing instructions that, when executed by the processor, configures the processor to
  acquire an image, recorded using an optical sensor, wherein the image has a field of view including at least the body region of the patient to be depicted via an X-ray image;
  determine at least one piece of patient-specific, body-related information for the patient from the acquired image;
  determine an X-ray attenuation distribution of the patient, at least for the body region to be depicted via the X-ray image, with reference to the determined at least one piece of patient-specific, body-related information; and
  determine the tube current profile with reference to the determined X-ray attenuation distribution.

At least one embodiment of the invention further relates to an X-ray image recording device for recording at least one X-ray image of a body region of a patient, comprising:
 an X-ray source;
 an X-ray detector; and
 a processor and a memory, embodied to determine a tube current profile for recording of at least one X-ray image of a body region of a patient with an X-ray image recording device, the memory containing instructions that, when executed by the processor, configures the processor to
  acquire an image, recorded using an optical sensor, wherein the image has a field of view including at least the body region of the patient to be depicted via an X-ray image;
  determine at least one piece of patient-specific, body-related information for the patient from the acquired image;
  determine an X-ray attenuation distribution of the patient, at least for the body region to be depicted via the X-ray image, with reference to the determined at least one piece of patient-specific, body-related information; and
  determine the tube current profile with reference to the determined X-ray attenuation distribution.

BRIEF DESCRIPTION OF THE DRAWINGS

The following describes and explains the invention in more detail with reference to the example embodiments shown in the figures, which show.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Further, although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

At least one embodiment of the invention is based on the acquisition of an image, which was recorded via an optical sensor. This image comprises at least the body region of a patient, which is to be depicted in an X-ray image, which is to be recorded with an X-ray image recording device. Furthermore, at least one piece of patient-specific, body-related information is derived from the image. The inventors have now recognized that the patient-specific, body-related information on the patient can be used to determine an X-ray attenuation distribution for the patient at least for the body region of the patient to be depicted by way of an X-ray image and use this to determine an X-ray tube current profile.

Here, the X-ray tube current profile, or in short tube current profile, is selected such that the dose applied to the patient during the recording of the X-ray image is as low as possible. In other words, the tube current profile is a dose-reducing tube current profile.

At least one embodiment of the invention is based on the consideration that, for a determination of an optimal X-ray tube current profile with respect to the X-ray dose, the individual X-ray attenuation properties of a patient can be determined without recording a topogram. Accordingly, the method according to at least one embodiment of the the invention for the determination of the X-ray attenuation distribution makes use of an image of the patient which was recorded with an optical sensor.

The optical sensor is designed to detect electromagnetic radiation reflected and/or emitted by the patient. The optical sensor is further designed to detect electromagnetic radiation in a low-frequency spectral region compared to X-rays, in particular in the visible or infrared spectral region. The optical sensor is embodied to generate a two-dimensional or a three-dimensional image.

Consequently, the patient is not exposed to any potentially hazardous additional X-rays during image recording with the optical sensor. This advantageously reduces the total dose to which the patient is exposed.

The field of view of the image recorded with the optical sensor is at least large enough for it to show the body region of the patient to be depicted by way of an X-ray image or to be scanned. Alternatively, the field of view of the image is large enough to show the patient completely or almost completely. In this case, the patient's body is depicted in the patient's entire longitudinal or width extension or only small regions of the body, are missing, for example the feet. This makes the determination of the at least one piece of patient-specific, body-related information from the image particularly accurate.

The acquisition of the image is preferably performed directly before the X-ray image recording or the X-ray scan, but this temporal relationship is not mandatory.

The image shows the patient preferably in the same position or posture as that adopted during the X-ray recording or the X-ray scan. This enables a particularly precise adaptation of the tube current profile to the X-ray attenuation distribution of the patient. During the acquisition of the image, the patient is preferably lying in a supine position and on the patient bed of the X-ray image recording device.

A piece of patient-specific, body-related information should be understood to mean each piece of information on a patient revealing details of the individual morphology or anatomy of the patient's body. In particular, this should be understood to mean the height of the patient, i.e. the patient's extension from head to foot along the patient's body axis, the patient's extension in the lateral direction, i.e. the patient's width, the patient's extension in the anterior-posterior direction, i.e. the patient's body depth or the patient's body surface. Other pieces of information on the patient's body, such as, for example, a specific tissue distribution, tissue composition, the position or height of certain organs or tissues, absolutely or relative to one another is also covered by this term.

According to a first aspect of at least one embodiment, the optical sensor records a three-dimensional image of the patient of at least the body region of the patient to be depicted. Accordingly, the optical sensor in this embodiment of the invention is designed for contactless sampling of the surface of an object. The three-dimensional image contains depth information on the image content depicted. In other words, the three-dimensional image also contains information on the distance of the patient from the sensor for each pixel or for each image point. Unlike the case with a two-dimensional image, which only depicts an object in two dimensions with grey values or color values, the three-dimensional image is particularly valuable due to its increased information content with respect to the at least one piece of patient-specific, body-related information.

According to a further aspect of at least one embodiment of the invention, at least one of the following pieces of patient-specific, body-related information is determined from the image recorded with the sensor: the body surface of the patient at least in the body region to be scanned, the patient's height or weight distribution.

Body surface should be understood to mean the three-dimensional area formed by the skin of the patient or clothing or a covering or the like lying thereupon separating the patient from the environment. Weight distribution should be understood to mean the distribution of mass according to the tissue density of the patient's body; it should in particular be understood to be the weight of the patient.

The acquisition of the surface of the patient can be restricted to the body region to be scanned, even if the image shows a larger field of view. This speeds up the computing process. The surface is preferably determined for the entire body or the entire region of the body depicted in order to be able to derive further pieces of patient-specific, body-related information particularly accurately. The acquisition of the body surface of the patient includes, for example, the derivation of a three-dimensional area model from the image. The derived information on its own or in any combination is now used to determine an X-ray attenuation distribution of the patient.

To this end, according to a further aspect of at least one embodiment, a reference dataset is selected from a plurality of reference datasets, which has the greatest possible conformity with respect to the at least one piece of patient-specific, body-related information on the patient. I.e. the reference dataset selected is the one which differs least from the patient with respect to the at least one piece of patient-specific, body-related information.

A reference dataset corresponds to data obtained via X-ray image recording device, in particular X-ray image recordings of a reference patient, wherein at least one piece of body-related information specific to the reference patient can be derived from each reference dataset. For example, it is also possible to extract the body surface of the reference patient from the reference dataset in the form of a three-dimensional area model. A reference patient should be understood to be a comparative patient for whom data obtained via the X-ray image recording device is available. A reference patient can be a medical phantom. The reference datasets correspond to X-ray projection data sets or X-ray image data sets which were obtained via any X-ray image recording device. These are kept available in a database or generally in a memory for evaluation and can for example be retrieved via a PACS ("Picture Archiving and Communication System").

The selection of the reference dataset is based on a comparison of only one piece or any combination of the pieces of patient-specific, body-related information. For example, it is performed exclusively with reference to the height, weight distribution or body surface. Preferably, two or all three comparative criteria are used in order to find the reference dataset of the reference patient with the most similar body structure to that of the patient.

According to a further aspect of at least one embodiment, at least one virtual topogram corresponding to a direction of projection is compiled from the selected reference dataset. Therefore, the virtual topogram corresponding to a direction of projection is calculated from the data available in the reference dataset, which was obtained via an X-ray recording device, and then an X-ray attenuation distribution corresponding to the direction of projection for the patient is derived therefrom and used in the following method step for the determination of the tube current profile.

This aspect of at least one embodiment is based on the consideration that the X-ray attenuation properties of the patient, which cannot be derived from the image recorded via optical sensor, can be approximately replaced by the X-ray attenuation properties of a patient with a comparable physical stature.

According to a further aspect of at least one embodiment, a virtual topogram is compiled in the lateral and/or anterior-posterior direction from the selected reference dataset and in each case a lateral and/or anterior-posterior X-ray attenuation distribution is derived from the virtual topogram. This is particularly suitable to be used by known automatic dose control systems for the determination of the dose-reducing tube current profile. A virtual topogram should be understood to be a topogram which is derived from the already existing data for the reference patient by suitable calculation steps.

A particularly good approximation of the X-ray attenuation distribution of the patient can be achieved according to a further aspect in that the selected reference dataset is modified before the compilation of the at least one virtual topogram such that the body surface of the reference dataset and the body surface of the patient substantially conform and the virtual topogram is compiled with reference to the modified reference dataset.

The modification of the reference dataset preferably comprises the deformation or shaping of the body surface of the reference dataset until the surface lines of the reference surface and body surface of the patient are identical or only deviate from one another within prespecified tolerances. This minimization of existing anatomical differences in the body surfaces of the patient and the reference patient advantageously reduces the differences in the X-ray attenuation.

According to a further aspect of at least one embodiment of the invention, the body surface of the reference dataset is elastically deformed. In other words, the shaping of the reference dataset to match the position and shape of tissues or organs in the body of the reference patient is extended so that the X-ray attenuation properties derived from the virtual topogram compiled on the basis of the modified reference dataset are even better adapted to the actual X-ray attenuation distribution of the patient.

According to a further, particularly expedient aspect of at least one embodiment, the modification of the reference dataset is performed at least partially by a user via an input device. This enables account to be taken of special patient-specific features. For example, an input device identifies movement, contact and/or speed of the user and derives commands for the modification therefrom. Alternatively, the modification takes place automatically.

According to a further aspect of at least one embodiment of the invention, the extension of the patient in the lateral and/or anterior-posterior direction along the body axis from the image at least for the body region to be depicted by way of an X-ray scan is derived as patient-specific, body-related information. In other words, the width and/or the depth of the patient are determined along the patient's body axis.

Lateral or anterior-posterior extension should in each case be understood to be the maximum extension of the patient in the corresponding direction for a position along the body axis of the patient.

In the way explained above, to this end, first, the body surface of the patient can be derived from the image. Then a consideration of the distance of each position along the body axis is used to derive values for the extension of the patient in the lateral and anterior-posterior directions.

For the determination of the lateral extension, it is alternatively possible to use a two-dimensional image of the patient, which was recorded in the anterior-posterior direction. For the determination of the anterior-posterior extension of the patient, it may be necessary to complete the three-dimensional body surface in those regions that are not depicted by the three-dimensional image.

According to a further aspect of at least one embodiment, the lateral and/or anterior-posterior X-ray attenuation distribution is calculated with reference to the extension of the patient and the X-ray attenuation capacity of water. While the X-ray attenuation properties of the patient are not known, the patient's width and/or depth in the region to be scanned and the X-ray attenuation due to water are known. The procedure described according to this inventive alternative of the method is based on the consideration that the X-ray attenuation behavior of the patient can be approximated if it is assigned the X-ray attenuation of water. In other words, the patient's tissue is approximated as water-equivalent tissue.

Here, the calculation of a lateral and/or anterior-posterior X-ray attenuation distribution also has the advantage that it is particularly suitable, i.e. without further adaptations of existing algorithms, for use by known automatic dose control systems for the determination of a dose-reducing tube current profile. Obviously, it is possible for the extension of the patient and corresponding X-ray attenuation distribution to be determined with reference to the body surface for any direction required.

According to a further aspect of at least one embodiment of the invention, the above-described approximation of the X-ray attenuation behavior of the patient is particularly suitable if the X-ray attenuation capacity of water is adapted in dependence on the body region of the patient to be depicted such that it takes account of the X-ray attenuation of at least one tissue type within the body region of the patient to be depicted with an X-ray attenuation different from that of water. This adaptation or correction can for example be performed with respect to pulmonary tissue and/or bone tissue since pulmonary tissue absorbs X-rays to a lesser degree than water and bone tissue absorbs X-rays more efficiently than water. A correction with respect to several tissue types and in particular other than those mentioned is also possible. Obviously, the correction can be performed along any projection direction. Values for a correction can, for example, be derived from reference datasets in each case containing data on a reference patient or phantom obtained via an X-ray image recording device.

According to a further aspect of at least one embodiment of the invention, a value for the averaged width along the patient's body axis at least in the body region to be depicted or scanned and/or the patient's height is determined from the image as patient-specific, body-related information on the patient. This patient-specific, body-related information can advantageously be determined from both a two-dimensional and a three-dimensional image. This aspect therefore permits a wide field of application for the invention. The averaged or average width is obtained if the width of the patient along his body axis is determined slice-by-slice and the mean value formed therefrom.

According to a further aspect of at least one embodiment, the patient is classified in at least one of a plurality of reference classes with reference to the value for the averaged patient width and/or the patient's height. A defined X-ray attenuation distribution is stored for each reference class. The X-ray attenuation distribution of the reference class in which the patient was classed is assigned to the patient.

According to a further aspect of at least one embodiment, each reference class includes a plurality of reference patients, wherein their values for the averaged patient width and/or the patient size of the reference patients of a reference class lie within a specific value range. For each reference patient in a reference class, at least one topogram or an image acquired by an optical sensor is available and can be used for the determination of the average width and/or height of the reference patient. In other words, a reference class is, for example, formed on the basis of topograms of the reference patients with an average width lying within specific limit values. Alternatively, a reference class is based on tomograms of reference patients with a height within a specific height range. In addition, a reference class can also be defined by more than only one piece of patient-specific, body-related information, for example by reference patients with an average width and height within defined value ranges. The classification of the patient in one of the reference classes is then performed by comparing the mean width and the height.

The topograms stored for each reference class are used in order to derive an X-ray attenuation distribution for each patient. Preferably, the X-ray attenuation distribution for a reference class corresponds to a mean value, in particular a weighted mean value, of the X-ray attenuation distributions of reference patients belonging to the reference class.

The procedure according to this aspect of at least one embodiment of the invention is based on the consideration that the X-ray attenuation distribution of the patient can be approximated as the mean value from X-ray attenuation distributions for reference patients with a comparable physical stature, in particular a comparable average width and/or height. While the exact X-ray attenuation distribution of the patient at least in the body region to be scanned is not known, there are a plurality of topograms and hence X-ray attenuation distributions for other patients. Under the assumption that the X-ray attenuation distributions of the patient and of reference patients with a comparable stature are very similar, an X-ray attenuation distribution averaged over the reference patients can also be used for the patient.

At least one embodiment of the invention further relates to a computer program with a program code for carrying out all method steps of the method according to the invention when the program is executed in a computer. This means the method can be carried out reproducibly and with little susceptibility to errors on different computers.

At least one embodiment of the invention further relates to a machine-readable data carrier on which the above-described computer program is stored.

At least one embodiment of the invention further relates to an X-ray image recording device with an X-ray source, an X-ray detector and a computer embodied to carry out a method according to at least one embodiment of the invention.

The X-ray image recording device is an X-ray apparatus, which is designed to record a plurality of X-ray projections from different projection angles, for example a computed tomography apparatus with an annular rotating frame or a C-arm X-ray apparatus. The recordings can be generated during a, in particular continuous, rotary movement of a recording unit with an X-ray source and an X-ray detector that interacts with the X-ray source. The X-ray source can in particular be an X-ray tube with a rotary anode. The X-ray detector for a computed tomography apparatus is, for example, a line detector with a plurality of lines. An X-ray detector for a C-arm X-ray apparatus is, for example, a flat panel detector. The X-ray detector can be embodied as both energy-resolving and counting.

According to a further aspect of at least one embodiment, the X-ray image recording device comprises the above-described optical sensor for recording an image of the patient at least in the body region to be depicted.

At least one embodiment of the invention further relates to an X-ray image recording device with an X-ray source, an X-ray detector and a computer, wherein the computer is embodied to acquire an image of a patient recorded via an optical sensor, wherein the image has a field of view including at least one body region to be depicted via X-ray image recording, to determine at least one piece of patient-specific, body-related information for the patient from the image, to determine an X-ray attenuation distribution of the patient at least for the body region to be depicted by way of an X-ray image with reference to the at least one piece of patient-specific, body-related information and to determine a tube current profile with reference to the X-ray attenuation distribution determined for the recording of the X-ray image.

The computer can further be embodied to prompt an optical sensor, for example by emitting control signals, to record the image of the patient.

Figure 1:
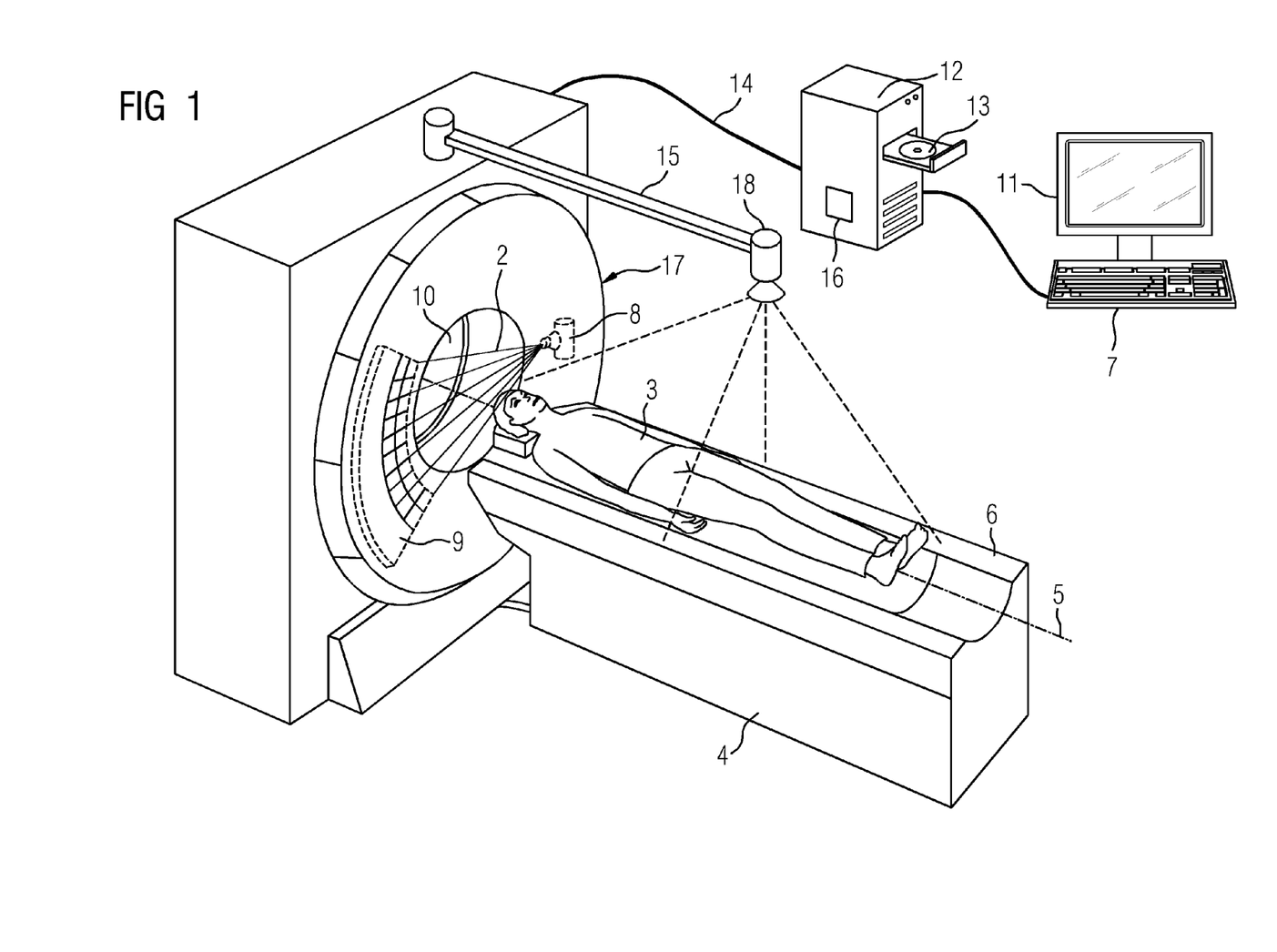
FIG. 1 an X-ray image recording device according to a example embodiment of the invention, FIG. 2 a schematic view of a three-dimensional image acquired via an optical sensor and a derived surface model, FIG. 3 a flowchart of the method according to the invention according to a first example embodiment, FIG. 4 a flowchart of the method according to the invention according to a second example embodiment and FIG. 5 a flowchart of the method according to the invention according to a further example embodiment.

FIG. 1 shows an X-ray image recording device using the example of an X-ray computed tomography device. The computed tomography device has a recording unit 17 comprising a radiation source 8 in the form of an X-ray source and a radiation detector 9 in the form of an X-ray detector. During the recording of X-ray projections, the recording unit 17 rotates about a system axis 5 and, during the recording, the X-ray source emits rays 2 in the form of X-rays. The X-ray source is an X-ray tube. The X-ray detector is a line detector with a plurality of lines.

During the recording of projections, a patient 3 lies on a patient bed 6. The patient bed 6 is connected to a base of the bed 4 which supports the patient bed 6 with the patient 3. The patient bed 6 is designed to move the patient 3 along a receiving direction through the opening 10 of the recording unit 17. The receiving direction is as a rule defined by the system axis 5 about which the recording unit 17 rotates during the recording of X-ray projections. In this example, the body axis of the patient is the same as the system axis 5. Both axes lie on the Z-axis of a three-dimensional, Cartesian coordinate system. In the case of a spiral recording, the patient bed 6 is moved continuously through the opening 10 while the recording unit 17 rotates about the patient 3 and records X-ray projections. In this way the X-rays describe a spiral on the surface of the patient 3.

The X-ray recording device has an optical sensor in the form of a camera 18. In this example, said camera is arranged above the patient bed 6 and fixed to the image recording device via a holding device 15. The camera 18 can also be attached to the rotatable recording unit 17. Alternatively, the camera 18 is arranged in a stationary or mobile fashion in the examination chamber with a clear view of the patient, for example on the roof of the examination chamber or is arranged on a stand which can be freely moved in the examination chamber. The camera 18 can be embodied as a two-dimensional camera that generates a two-dimensional depiction of an object in grey steps or color values. In this example, the camera 18 is embodied as a three-dimensional camera, for example in the form of a stereo camera, time-of-flight camera or as an interferometric device or the like, and comprises components required for the respective recording technique, such as suitable light sources and detection units.

The X-ray image recording device has a computer 12, which is connected to a display unit 11, for example for the graphical display of X-ray recordings and an input unit 7. The display unit 11 can, for example, be an LCD, plasma or OLED screen. It can furthermore be a touch-sensitive screen, which is also embodied as an input unit 7. A touch-sensitive screen of this kind can be integrated in the imaging apparatus or as part of a mobile apparatus. The input unit 7 is, for example, a keyboard, a mouse, a so-called "touch screen" or even a microphone for voice input. The input unit 7 can also be configured to recognize movements of a user and translate them into corresponding commands. The input unit 7 can, for example, be used by a user to modify a selected reference dataset.

The computer 12 is connected to the rotatable recording unit 17 for the exchange of data. The connection 14 is used, on the one hand, to transmit control signals for the X-ray image recording from the computer 12 to the recording unit 17 and, on the other, to transmit recorded projection data for image reconstruction to the computer 12. The connection 14 is implemented in a known way either with a cable connection or wirelessly. The computer 12 is further also connected to the camera 18 for the exchange of control signals or image data, in particular via the same connection 14.

The computer 12 comprises a computing unit 16. The computing unit 16 is embodied as an image or image data processing unit. It is configured to carry out all the computing steps relating to the method according to the invention on the image recorded by the camera 18 and/or reference data. The computing unit 16 can interact with a computer-readable data carrier 13, in particular to carry out a method according to the invention by way of a computer program with a program code. Furthermore, the computer program can be stored for retrieval on the machine-readable carrier.

In particular, the machine-readable carrier can be a CD, DVD, a Blu-ray disk, a memory stick or a hard disk. The computing unit 16 can be embodied in the form of hardware or in the form of software. For example, the computing unit 16 is embodied as a so-called FPGA (abbreviation "Field Programmable Gate Array") or comprises an arithmetic logic unit.

In the embodiment shown here, at least one computer program is stored on the memory of the computer 12, which carries out all method steps of the method according to the invention when the computer program is executed on the computer 12. The computer program for the execution of the method steps of the method according to the invention comprises a program code. The computer program can furthermore be embodied as an executable file and/or stored on a different computing system than the computer 12. For example, the X-ray image recording device can be designed such that the computer 12 loads the computer program to execute the method according to the invention into its internal working memory via an intranet or via the Internet.

Figure 2:
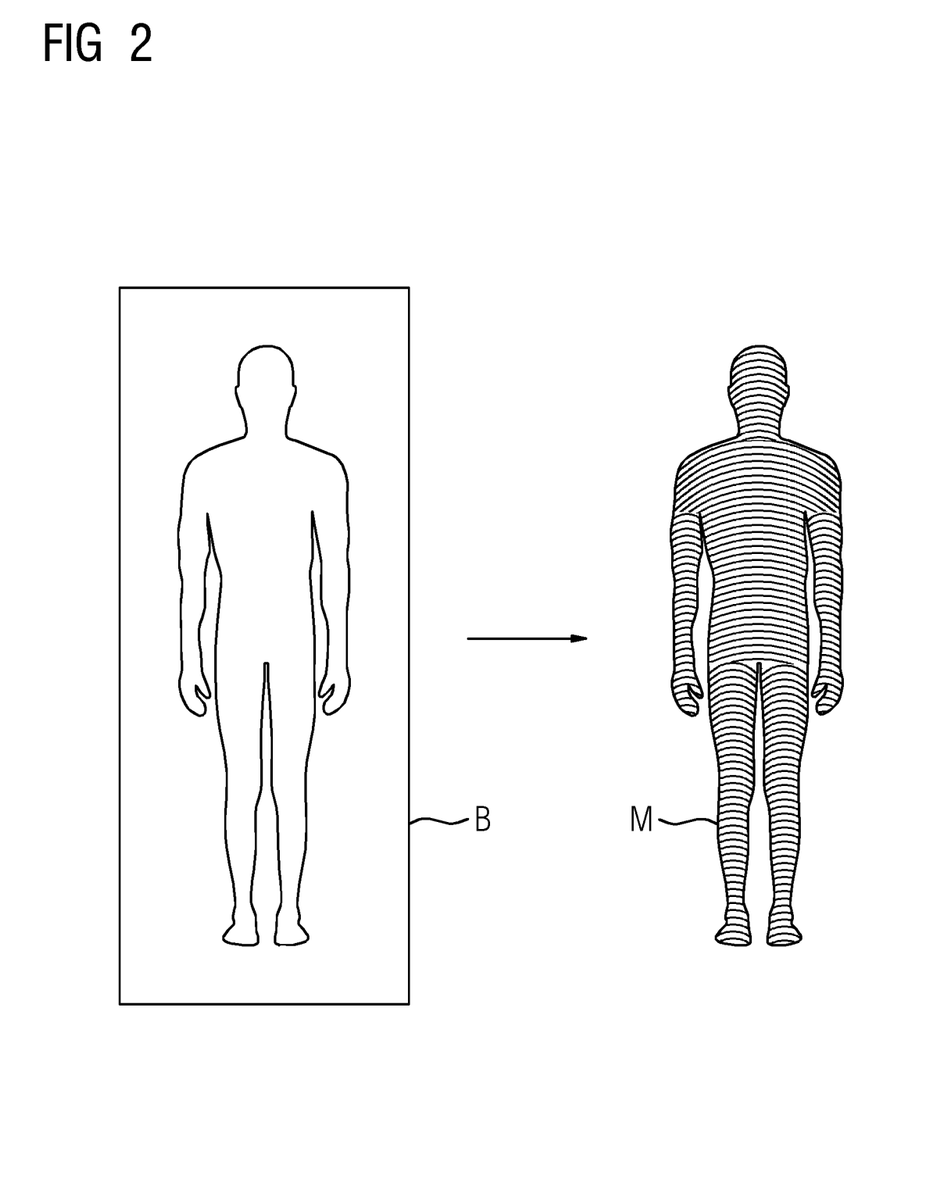
Figure 3:
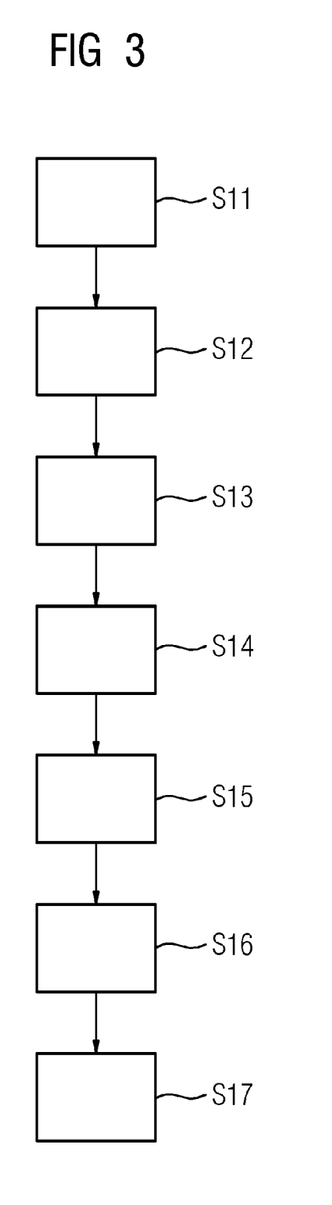

FIG. 3 describes a first example embodiment of the method according to an embodiment of the invention. In a first step S11, the computing unit 16 of the computer 12 receives a three-dimensional image B of a patient 3 lying in the supine position on the patient bed 6, as shown schematically in FIG. 2. The image B was recorded via the camera 18 and shows the patient 3 completely. In addition to the contour of the patient 3, the three-dimensional image B also contains depth information with respect to the three-dimensional surface structure of the patient 3. As a result, the shape or configuration of the surface of the patient 3 is also acquired.

In step S12, three pieces of patient-specific, body-related information are derived from the image B.

The computing unit 16 extracts the three-dimensional surface of the patient from image B in that it transfers the depth information into a three-dimensional surface model M, which is also shown schematically in FIG. 2. To this end, for example a clouds of points representing the surface shape is interpolated to form a smooth three-dimensional surface, which is then described by a model, for example by way of a series of triangles. Alternatively, the area model M describes the area contour formed by the skin slice-by-slice along the body axis of the patient 3, as shown in FIG. 2. The computing unit 16 determines the height of the patient 3 for example by finding the two points lying on the surface model M with the greatest distance from one another along the body axis. In addition, a weight estimation is performed with reference to the surface model M. To this end, the surface model M is supplemented with respect to the missing regions of the surface of the patient which are not shown in the three-dimensional image B—in this example, the patient's back is missing—in order to obtain a complete, in other words, enclosed, three-dimensional surface model. This is performed with known extrapolation methods or with the aid of a three-dimensional model of the patient bed, which is inserted by the computing unit 16 into the area model M. The weight of the patient 3 is determined assuming a density for the patient's body.

In a third step S13, the computing unit 16 selects a particularly suitable reference dataset with respect to the height and the weight of the patient. To this end, the computing unit 16 resorts to a pool of reference datasets, which is stored in the memory of the computer 12 or on an external data carrier that can be connected to the computer 12 or can be retrieved via an intranet or internet from a central memory, for example via a PACS. The computing unit 16 selects the dataset for the reference patient which is most similar to the patient with respect to height and weight. To this end, the height and weight information is already provided in the reference dataset as extracted information or the computing unit 16 determines these heights from the reference dataset by way of suitable processing steps. For example, the reference data is converted by forward projection and/or backward projection steps into a form which enables the derivation of the height and weight distribution of the reference patient. Taking account of two criteria, instead of only one criterion, during the selection achieves better anatomical conformity between the selected reference dataset and the patient 3.

In addition, a surface model of the reference patient is derived from the reference data, for example by way of known segmentation techniques.

In a fourth step S14, a modification of the reference dataset is performed corresponding to an adaptation of the reference data to the anatomy of the patient. Although the reference patient and the patient have a comparable height and weight distribution, they do not necessarily also have to have a comparable X-ray attenuation distribution. The adaptation achieves a better approximation of the X-ray attenuation distribution.

Since the reference data is data obtained with any X-ray recording device, the spatial relationship between the reference data and the surface model acquired by the camera 18 is as a rule unknown. This has to be established subsequently. The geometric relationship is determined by the computing unit 16 with reference to a suitable registration of the surface models for the patient 3 and the reference patient. The display unit 11 shows a user the surface models in superimposed form. The user now minimizes deviations in the surface contour by marking regions of the reference model with the cursor and mouse and displacing them in the direction of the patient model M by moving the mouse. The computing unit 16 then applies corresponding transformation steps in real time to the reference dataset. Alternatively, the modification of the reference dataset is performed automatically in the following way: the computing unit 16 considers the two area models slice-by-slice and determines the surface contour formed by the skin for the patient 3 and the reference patient in each slice. An elastic registration of the reference contour to the contour of the patient 3 produces a deformation vector field, which is then continued smoothly into the interior of the reference patient.

In step S15, the computing unit 16 uses forward projection in the lateral and anterior-posterior directions to calculate two virtual topograms from the modified reference dataset, and in step S16, said virtual topograms are transferred by way of an evaluation of the grey value distribution into an X-ray attenuation distribution in the form of an X-ray attenuation vector in the lateral and anterior-posterior directions, $A_{lat}(z)$ and $A_{ant}(z)$. The computing unit 16 uses these X-ray attenuation distributions as the basis for executing an automatic dose control system for determining a dose-reducing tube current profile for the following X-ray image recording. At the same time, the user uses the input unit 7 to provide information on the medical question underlying the X-ray image recording medical question or on reference values for X-ray attenuation and tube current corresponding to a desired image quality. Alternatively, the display unit 11 provides the user with corresponding suggestions for selection.

According to this example embodiment, the automatic dose control system determines a tube current modulation for the X-ray image recording of the body region to be depicted, which is angle-dependent, i.e. projection-direction-dependent, and dependent on the position along the body axis of the patient 3.

Figure 4:
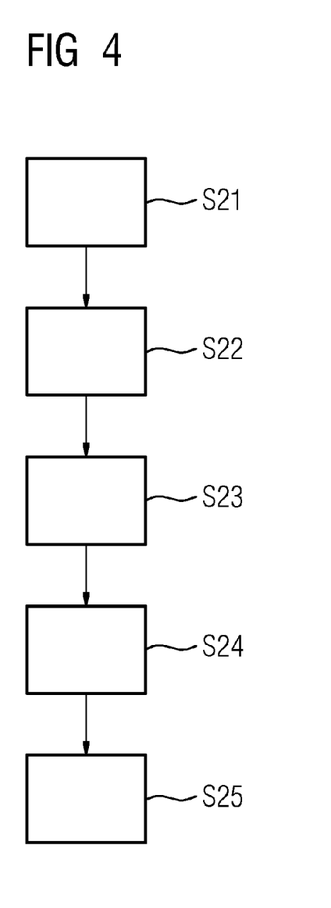

FIG. 4 shows a further example embodiment of the method according to the invention, according to which, in first and second steps S21 and S22, a three-dimensional image B of a patient 3 is acquired or determined with a camera 18 and hence also the surface shape of the patient 3 and a corresponding representation of the surface as an area model M. For the specific procedure with respect to these steps, reference is made to the explanations for steps S11 and S12 in FIG. 3. In this example embodiment, the surface model M is once again supplemented by the missing parts of the three-dimensional image B in order to obtain the complete surface of the patient. In step S23, the width or the depth of the patient 3 in lateral and anterior-posterior directions, $L_{lat}(z)$ and $L_{ant}(Z)$ is now obtained for each position z along the body axis from the surface model M and used in order to calculate an X-ray attenuation distribution in the form of a lateral or anterior-posterior X-ray attenuation vector, $A_{lat}(z)$ or $A_{ant}(z)$, according to the formula $$A(z)=\exp(\mu*L(z))$$

where μ designates the X-ray absorption coefficients of water. This approximation of the X-ray attenuation due to the patient 3 is improved in that the lateral or anterior-posterior X-ray attenuation vector, $A_{lat}(z)$ or $A_{ant}(z)$, is calculated according to the formula $$A(z)=\exp(\mu*L(z)*K(z))$$

where K(z) is a correction profile for the lateral or anterior-posterior direction taking into account the X-ray attenuation properties of lung tissue and bone tissue in the body region to be depicted, which differ from those of water.

The computing unit 16 determines the correction profile K(z) from a plurality of reference datasets, in each case including data on a reference patient obtained via the X-ray image recording device. To this end, the computing unit 16 selects the reference dataset with reference to the greatest possible anatomical conformities between the reference patient and the patient and determines correction values from the reference data. The reference data can be stored in the memory of the computer 12, on an external data carrier that can be connected to the computer 12 or in a central memory (PACS) that can be reached by intranet or internet. In step S25, the lateral and anterior-posterior X-ray attenuation vectors, $A_{lat}(z)$ and $A_{ant}(z)$ are taken into account by automatic dose control system for the calculation of a dose-reducing tube current profile. According to this example embodiment, the automatic dose control system also determines an angle-dependent and z-position-dependent tube current profile for the X-ray image recording of the body region to be depicted. In other words, the automatic dose control system determines, in dependence on the X-ray attenuation distribution of the patient for each position along the patient's body axis and/or each direction of projection, the values for the tube current which provide sufficient image quality to answer the medical question.

Figure 5:
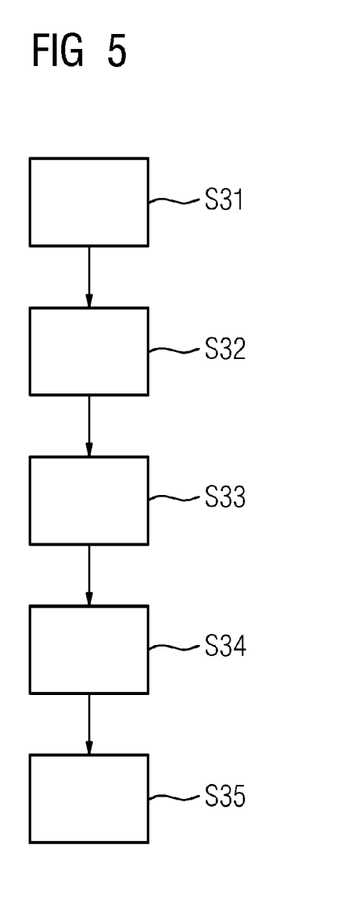

According to a third example embodiment of the invention shown in FIG. 5, in step S31, a three-dimensional or two-dimensional image of a patient is acquired via the camera 18. In step S32, the computing unit 16 extracts the average width and the height of the patient from the image. To this end, it evaluates either the external contour of the patient in the two-dimensional image or uses a surface extracted from the three-dimensional image in a known manner. A plurality of topograms on reference patients which are sorted into in reference classes according to height and average width are stored on the memory of the computer 12 or an external memory, which can be reached via the intranet or internet, for example via a PACS. For example, the following reference classes are provided: "large-corpulent", "large-slender", "small-normal", "medium-slender" and the like. The patient is assigned to the "large-slender" reference class according to the patient's height and average width in step S34. For this reference class, an X-ray attenuation distribution is stored which is obtained as averaging over the X-ray attenuation distribution of all the reference patients belonging to the class. This averaged X-ray attenuation distribution is assigned to the patient in step S34 and used in step S35 for the determination of a dose-optimized tube current profile. According to this example embodiment, a constant tube current corresponding to the averaged X-ray attenuation over the body axis of the patient is selected for the X-ray image recording of the body region to be depicted.

FIG. 2 shows by way of example a three-dimensional image B, which was acquired with a camera 18 and the field of view of which includes the entire body of the patient. This enables patient-specific, body-related information to be determined particularly accurately, however this requires increased computing effort. Alternatively, the compilation of a three-dimensional surface model M from the three-dimensional image B can be restricted to the body region to be depicted or a larger body region encompassing the body region to be depicted, and then the same applies to the acquisition of surfaces in reference datasets. This is followed by an assessment of height and/or weight with reference to the detection of so-called anatomical landmarks, such as, for example, head, chin, shoulders, hips, knee, feet or the like. An estimation of the height and weight of the patient is performed in the same way for a two-dimensional or three-dimensional image with reference to anatomical landmarks, when the field of view of the image acquired by the camera 18 does not completely acquire the patient 3.

In order to be able to derive the at least one piece of patient-specific, body-related information with high precision from the image B recorded via the optical sensor, a second image can be recorded with the camera 18. This shows the same field of view as the first image B acquired with the optical sensor, but without the patient 3. This second image can be used to calibrate the first image with the patient. Advantageously, one calibration can be applied to all variants of the method according to at least one embodiment of the invention.

For example, calibration of the first image 3 includes the removal of image contents that do not relate to the patient 3, such as, for example, information on the patient bed or the examination chamber. This is performed in that the second image is subtracted pixel for pixel from the first image 3.

The aforementioned description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods. Further, elements and/or features of different example embodiments may be combined with each other and/or substituted for each other within the scope of this disclosure and appended claims.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Further, at least one embodiment of the invention relates to a non-transitory computer-readable storage medium comprising electronically readable control information stored thereon, configured in such that when the storage medium is used in a controller of a magnetic resonance device, at least one embodiment of the method is carried out.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a tube current profile for recording of at least one X-ray image of a body region of a patient with an X-ray image recording device, the x-ray image recording device including a processor and a memory, the method comprising:
   acquiring, via an optical sensor, an image having a field of view including at least the body region of the patient to be depicted via an X-ray image;
   determining, via the processor, at least one piece of patient-specific, body-related information for the patient from the acquired image;
   selecting a reference dataset from a plurality of reference datasets based on the at least one piece of the patient-specific, body-related information, the reference datasets each including data on a reference patient;
   compiling at least one virtual topogram corresponding to a respective X-ray projection direction from the selected reference dataset;
   determining, via the processor, an X-ray attenuation distribution of the patient, at least for the body region to be depicted via the X-ray image, with reference to the at least one virtual topogram;
   determining, via the processor, the tube current profile with reference to the X-ray attenuation distribution such that the tube current profile is determined without exposing the patient to x-rays; and
   setting, via the processor, a tube current of an imaging system based on the tube current profile.

2. The method of claim 1, wherein the image is a three-dimensional image.

3. The method of claim 1, wherein the determining of at least one piece of patient-specific, body-related information for the patient includes acquiring at least one of the following pieces of patient-specific, body-related information from the image: a body surface of the patient at least in the body region to be depicted, the patient's height distribution and the patient's weight distribution.

4. The method of claim 3, wherein the selecting the reference dataset comprises:
   selecting the reference data set from the plurality of reference datasets such that the reference data set has a greatest possible conformity with respect to at least one piece of the patient-specific, body-related information, wherein the data on the reference patient is obtained via an X-ray image recording device from each piece of which at least one piece of patient-specific, body-related information for the reference patients is derivable.

5. The method of claim 1, wherein, in the compiling, a virtual topogram is compiled in at least one of the lateral and anterior-posterior direction and,
   the X-ray attenuation distribution includes at least one of a lateral and an anterior-posterior X-ray attenuation distribution is derived from the respective virtual topogram.

6. The method of claim 1, further comprising:
   modifying, before the compiling, the selected reference such that the body surfaces of the reference patient and patient substantially conform and, in the compiling, the at least one virtual topogram is compiled with reference to the modified reference dataset.

7. The method of claim 6, wherein the modifying comprises:
   elastic deformation of the body surfaces of the reference patient.

8. The method of claim 6, wherein the modification is performed at least partially by a user with aid of an input device.

9. The method of claim 1, wherein the determining of at least one piece of patient-specific, body-related information for the patient includes determining the extension of the patient in at least one of the lateral and anterior-posterior direction along the body axis at least in the body region of the patient to be depicted from the image.

10. The method of claim 9, wherein the determining of the X-ray attenuation distribution of the patient includes calculating at least one of a lateral and anterior-posterior X-ray attenuation distribution with reference to the values for the extension of the patient and of the X-ray attenuation capacity of water.

11. The method of claim 10, wherein the X-ray attenuation capacity of water is adjusted in dependence on the body region of the patient to be depicted so as to take account of the X-ray attenuation of at least one tissue type within the body region of the patient to be depicted with an X-ray attenuation different from that of water.

12. The method of claim 1, wherein, in the determining of the at least one piece of patient-specific, body-related information for the patient, at least one of
   a value for a width of the patient averaged along the patient's body axis is determined at least in the body region to be depicted, and
   a value for the patient's height is determined from the image.

13. The method of claim 12, wherein the determining of the X-ray attenuation distribution of the patient includes:
   classifying the patient in at least one of a plurality of reference classes with reference to the value of at least one of the averaged patient width and the patient height, and wherein a defined X-ray attenuation distribution is stored for each reference class; and
   assigning the X-ray attenuation distribution of the reference class to the patient in which the patient was classed.

14. The method of claim 13, wherein each reference class is formed from a plurality of reference patients whose values for at least one of the averaged patient width and the patient height lie within a specific value range.

15. A method of claim 13, wherein the X-ray attenuation distribution for each reference class corresponds to the mean value for the X-ray attenuation distributions for reference patients belonging to the reference class.

16. A non-transitory computer readable medium, including program code that when executed on a processor, causes a system including same to perform the method of claim 1.

17. A non-transitory machine-readable data carrier on which the non-transitory computer readable medium of claim 16 is stored.

18. The method of claim 2, wherein the determining of at least one piece of patient-specific, body-related information for the patient includes acquiring at least one of the following pieces of patient-specific, body-related information from the image: a body surface of the patient at least in the body region to be depicted, the patient's height distribution and the patient's weight distribution.

19. The method of claim 18, wherein the determining of the X-ray attenuation distribution of the patient includes selecting a reference dataset from a plurality of reference datasets with the greatest possible conformity with respect to at least one piece of the patient-specific, body-related information, wherein each reference dataset comprises data on a reference patient obtained via an X-ray image recording device from each piece of which at least one piece of patient-specific, body-related information for the reference patients is derivable.

20. The method of claim 5, wherein, before the compiling, the selected reference dataset is modified such that the body surfaces of the reference patient and patient substantially conform and, in the compiling, the at least one virtual topogram is compiled with reference to the modified reference dataset.

21. The method of claim 2, wherein the determining of at least one piece of patient-specific, body-related information for the patient includes determining the extension of the patient in at least one of the lateral and anterior-posterior direction along the body axis at least in the body region of the patient to be depicted from the image.

22. The method of claim 2, wherein, in the determining of the at least one piece of patient-specific, body-related information for the patient, at least one of
a value for a width of the patient averaged along the patient's body axis is determined at least in the body region to be depicted, and
a value for the patient's height is determined from the image.

23. A method of claim 14, wherein the X-ray attenuation distribution for each reference class corresponds to the mean value for the X-ray attenuation distributions for reference patients belonging to the reference class.

24. An X-ray image recording device for recording at least one X-ray image of a body region of a patient, comprising:
an X-ray source;
an X-ray detector; and
a processor and a memory, embodied to determine a tube current profile for recording of at least one X-ray image of a body region of a patient with an X-ray image recording device, the memory containing instructions that, when executed by the processor, configures the processor to,
acquire an image, recorded using an optical sensor, wherein the image has a field of view including at least the body region of the patient to be depicted via an X-ray image;
determine at least one piece of patient-specific, body-related information for the patient from the acquired image;
select a reference dataset from a plurality of reference datasets based on the at least one piece of the patient-specific, body-related information, the reference datasets each including data on a reference patient;
compile at least one virtual topogram corresponding to a respective X-ray projection direction from the selected reference dataset;
determine an X-ray attenuation distribution of the patient, at least for the body region to be depicted via the X-ray image, with reference to the at least one virtual topogram;
determine the tube current profile with reference to the determined X-ray attenuation distribution such that the tube current profile is determined without exposing the patient to x-rays; and
set a tube current of an imaging system based on the tube current profile.

25. The X-ray image recording device of claim 24, further comprising an optical sensor.

26. An X-ray image recording device for determining a tube current profile for recording at least one X-ray image of a body region of a patient comprising:
an X-ray source;
an X-ray detector; and
a processor and a memory, the memory containing instructions that, when executed by the processor, configures the processor to
acquire an image of a patient recorded via an optical sensor, wherein the image has a field of view including at least one body region to be depicted by way of X-ray image recording,
determine at least one piece of patient-specific, body-related information for the patient from the image,
select a reference dataset from a plurality of reference datasets based on the at least one piece of the patient-specific, body-related information, the reference datasets each including data on a reference patient,
compile at least one virtual topogram corresponding to a respective X-ray projection direction from the selected reference dataset,
determine an X-ray attenuation distribution of the patient, at least for the body region to be depicted by way of an X-ray image with reference to the at least one virtual topogram,
determine the tube current profile with reference to the X-ray attenuation distribution determined for the recording of the X-ray image such that the tube current profile is determined without exposing the patient to x-rays, and
set a tube current of an imaging system based on the tube current profile.

* * * * *